United States Patent [19]
Forget et al.

[11] Patent Number: 5,905,057
[45] Date of Patent: May 18, 1999

[54] HERBICIDAL 4-BENZOYLISOXAZOLE-3-CARBOXYLATE LIQUID COMPOSITIONS COMPRISING N-ALKYLPYRROLIDINONE STABILIZER

[75] Inventors: Jacqueline Forget, Lyons, France; David Alan Long, Chapel Hill, N.C.; Gilbert Antoine Perez, Sathonay-Camp, France

[73] Assignee: Rhone-Poulenc Agrochimie, Lyon Cedex, France

[21] Appl. No.: 08/965,194

[22] Filed: Nov. 6, 1997

[51] Int. Cl.[6] .......................... A01N 25/22; A01N 43/80
[52] U.S. Cl. .............................. 504/116; 504/271
[58] Field of Search ...................... 504/271, 116

[56] References Cited

U.S. PATENT DOCUMENTS

| | | | |
|---|---|---|---|
| 4,983,210 | 1/1991 | Rheinheimer et al. | 71/94 |
| 5,371,063 | 12/1994 | Cramp et al. | 504/270 |
| 5,371,064 | 12/1994 | Cramp et al. | 504/271 |
| 5,627,131 | 5/1997 | Shribbs et al. | 504/105 |
| 5,656,573 | 8/1997 | Roberts et al. | 504/271 |

FOREIGN PATENT DOCUMENTS

| | | |
|---|---|---|
| 0304409 | 2/1989 | European Pat. Off. . |
| 0418175 | 3/1991 | European Pat. Off. . |
| 0487357 | 5/1992 | European Pat. Off. . |
| 0527036 | 2/1993 | European Pat. Off. . |
| 0560482 | 9/1993 | European Pat. Off. . |
| 94/14782 | 7/1994 | WIPO . |
| 97/34486 | 9/1997 | WIPO . |

*Primary Examiner*—S. Mark Clardy
*Attorney, Agent, or Firm*—Burns, Doane, Swecker & Mathis, L.L.P.

[57] ABSTRACT

The invention relates to a liquid composition comprising:
  (a) a herbicidally effective amount of at least one alkyl 4-benzoylisoxazole-3-carboxylate derivative; and
  (b) at least one N-alkylpyrrolidinone derivative,
said composition being substantially stable.

14 Claims, No Drawings

HERBICIDAL 4-BENZOYLISOXAZOLE-3-CARBOXYLATE LIQUID COMPOSITIONS COMPRISING N-ALKYLPYRROLIDINONE STABILIZER

BACKGROUND OF THE INVENTION

This invention relates to novel herbicidal compositions comprising an alkyl 4-benzoylisoxazole-3-carboxylate derivative derivative and an N-alkylpyrrolidinone.

DISCUSSION OF RELATED ART

Herbicidal 4-benzoylisoxazoles are disclosed in the literature, for example see European Patent Publication Nos. 0418175, 0487357, 0527036 and 0560482 and Cramp et al U.S. Pat. No. 5,371,064. These compounds are highly active herbicides. A problem which may exist for these compound is their instability under certain conditions, for example as described in WO97/34486. This publication describes the use of sulfonic acid derivatives to stabilize 4-benzoylisoxazoles in the presence of partner pesticides, and in particular isoxaflutole [5-cyclopropyl-4-(2-methylsulfonyl-4-trifluoromethyl)benzoylisoxazole]. It is also stated that in this publication that the presence of N-methylpyrrolidinone as a solvent in emulsifiable concentrates containing the 4-benzoylisoxazoles tends to reduce the stability of the compositions. However, N-alkylpyrrolidinones are very useful in formulation chemistry, especially as primary solvents in the preparation of liquid formulations, in particular emulsifiable concentrates. They may also be useful as an adjuvant, improving or enhancing the availability of active ingredients when applied to plants.

Therefore the present invention seeks to provide compositions comprising a herbicidal 4-benzoylisoxazole and a primary solvent which possess improved stability properties over those of the prior art.

SUMMARY OF THE INVENTION

The present invention provides a liquid composition comprising:
(a) a herbicidally effective amount of at least one alkyl 4-benzoylisoxazole-3-carboxylate derivative; and
(b) at least one N-alkylpyrrolidinone derivative;
said composition being substantially stable.

Surprisingly, the applicants have found that alkyl 4-benzoylisoxazole-3-carboxylate derivatives may be used in combination with an N-alkylpyrrolidinone with significantly lower degradation of the alkyl 4-benzoylisoxazole-3-carboxylate in comparison with known 4-benzoylisoxazoles.

DESCRIPTION OF PREFERRED EMBODIMENTS

It will be understood that in this description the term 'liquid' includes thickened liquids and gels. Preferred formulations are emulsifiable concentrates, suspo-emulsions, and emulsion concentrates (e.g. either oil-in-water or water-in-oil emulsions). Compositions in the form of emulsifiable concentrates are particularly preferred.

The N-alkylpyrrolidinone is generally an N-($C_{1-20}$ alkyl) pyrrolidinone. preferably selected from N-octylpyrrolidinone or, most preferably N-methylpyrrolidinone (referred to in the description that follows as 'NMP').

Preferably the alkyl 4-benzoylisoxazole-3-carboxylate derivative has the general formula (I):

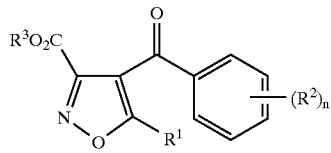

(I)

wherein
$R^1$ is $C_{1-6}$ alkyl or $C_{3-6}$ cycloalkyl optionally substituted by $C_{1-6}$ alkyl,
$R^2$ is selected from halogen, nitro, —S(O)$_p R^6$, —(CR$^4$R$^5$)$_q$ S(O)$_p R^6$, —N(R$^7$)SO$_2$R$^6$, $C_{1-6}$ alkoxy, —OSO$_2$R$^6$, $C_{1-6}$ halolkoxy, $C_{1-6}$ alkyl and $C_{1-6}$ haloalkyl;
n is one, two or three: p is zero, one or two;
$R^3$ is $C_{1-6}$ alkyl;
$R^4$ and $R^5$ independently are hydrogen or $C_{1-4}$ alkyl:
q is one or two: when q is two the groups —(CR$^4$R$^5$)— may be the same or different;
$R^6$ is $C_{1-6}$ alkyl, or phenyl optionally bearing from one to five substituents which may be the same or different selected from halogen, $C_{1-6}$ alkyl, $C_{1-6}$ alkoxy, $C_{1-6}$ haloalkyl, $C_{1-6}$ haloalkoxy, nitro and —S(O)$_p$CH$_3$;
and $R^7$ is hydrogen or $C_{1-6}$ alkyl;
or an agriculturally acceptable salt thereof.

Compounds of formula (I) in which $R^1$ is cyclopropyl are preferred.

Compounds of formula (I) in which n is three and the groups (R$^2$)$_n$ occupy the 2,3 and 4-positions of the benzoyl ring; or in which n is two and the groups (R$^2$)$_n$ occupy the 2 and 4-positions of the benzoyl ring are preferred.

Compounds of formula (I) above in which $R^2$ is halogen, —S(O)$_p$Me, trifluoromethyl, $C_{1-4}$ haloalkoxy, $C_{1-4}$ alkoxy or —CH$_2$S(O)$_p$Me. More preferably, $R^2$ is halogen, —S(O)$_p$e or trifluoromethyl.

Preferably one of the groups $R^2$ is —S(O)$_p$Me.
$R^3$ is preferably $C_{1-4}$ alkyl, more preferably methyl or, most preferably, ethyl.

Preferred compounds of formula (I) are ethyl 5-cyclopropyl-4-(2-methylsulfonyl-4-trifluoromethyl) benzoylisoxazole-3-carboxylate, and ethyl 5-cyclopropyl-4-(3,4-dichloro-2-methylsulfenyl)benzoylisoxazole-3-carboxylate, referred to hereafter as Compounds A and B respectively. Compound A is most preferred.

Compounds of formula (I) are known or can be prepared by known methods, for example see EP0487357, EP560482, WO94/14782, and U.S. Pat. Nos. 5,371,064; 5,371,063; 5,371,064 and 5,656,573.

In the description that follows, unless otherwise specified, the percentages are by weight.

The composition of the invention generally contains up to about 90%, especially up to about 75%, of active ingredients although it will be understood that this amount may vary depending on the nature of the composition and the solubility and/or dispersibility of the various components. Preferably the composition contains up to about 55% of active ingredients, more preferably from about 20 to about 55%. The amount of N-alkylpyrrolidinone present will normally be sufficient to dissolve the active ingredient presents.

It will be understood that in certain cases the stability of the partner pesticide may also depend on factors such as pH, and that the pH of the mixture may need to be adjusted by the skilled worker accordingly. Preferably the pH of a 1% solution of the composition in distilled water is from about 4 to about 8.

When in the form of an emulsifiable concentrate the composition may include an additional primary solvent [to aid dissolution of the isoxazole component (a), although in some cases it is also needed to dissolve a partner pesticide where present], which is a generally a polar solvent. Suitable primary solvents include ether solvents (e.g. tetrahydrofuran); dimethyl phthalate; acetonitrile; ketone solvents (e.g. butyrolactone, acetophenone, isophorone or cyclohexanone); and phosphates (e.g. tributyl or triethyl phosphates). Particularly preferred primary solvents are ketones, most preferably cyclohexanone or acetophenone.

The emulsifiable concentrate compositions of the invention typically include a secondary solvent, to help achieve a good emulsion on dilution, as well as keeping the cost of the composition lower (since such solvents are typically cheaper than the primary solvent). The secondary solvent can also, in some cases, contribute to the solvency of the composition. This secondary solvent is usually non-polar, and representative examples of suitable secondary solvents include aromatic solvents such as Exxon Aromatic 100, Aromatic 150 or Aromatic 200 (trade marks); chlorinated solvents such as chlorinated hydrocarbons (e.g. dichloromethane) and chlorinated aromatic solvents (e.g. chlorinated toluenes: mono- or dichlorobenzenes: or mixtures thereof); and esters such as $C_{8-18}$ (preferably $C_{8-10}$) methylated fatty acids, aromatic esters and methyl salicylate; and ethers. In addition, it has been found that in certain cases, mixtures of two or more secondary solvents (e.g. a methylated fatty acid and chlorinated aromatic solvents) can give particularly stable compositions.

It is also generally desirable to include one or more surfactants in the composition of the invention, which aid the availability of the active ingredient to the weeds to be controlled. Suitable surfactants include:

non-ionic surfactants, such as carboxylated alkyl phenols, alkoxylated alcohols, fatty acid alkoxylates, sorbitol and sorbitan alkoxylates and esters, block co-polymers, alkyl phenol alkoxylates, amine alkoxylates. alcohol ethers, alcohol alkoxyiates, alkoxylated vegetable oils (e.g. caster oil), and alkoxylated tristyrylphenols (e.g. ethoxylated tristyryl phenols); the latter being most preferred;

and ionic surfactants, especially anionic surfactants. In emulsifiable concentrates preferred ionic surfactants include phosphates esters which may be aryl alkoxylated, alcohol alkoxylated, and triaryl alkoxylated; sulfosuccinates; and sulfonic acid derivatives (e.g. the calcium salt).

The surfactants are preferably present in an amount from about 0.01 to about 20% of the composition weight, especially in emulsifiable concentrate formulations, preferably from about 2 to about 6% (e.g. about 2 to about 5%).

The compositions of the invention may also include one or more additional additives, which may be a fertilizers or pesticides, fungicide, an insecticide, a plant growth regulator or (preferably) a herbicide. Where an additional herbicide is present is preferably selected from a chloroacetamide herbicide (preferably selected from acetochlor, metolachlor, alpha-metolachlor, propalachlor, alachlor, dimethenamid, and (S)-dimethenamid); fluthiamid [N-isopropyl-(5-trifluoromethyl-1,3,4-thiadiazol-2-yl)-4-(4-fluoro-oxyacetanilide]; a triazine herbicide (e.g. terbuthylazine, terbutryn, simazine, cyanazine, atrazine and metribuzin, most preferably atrazine); a 2,6-dinitroaniline herbicide (e.g. trifluralin {2,6-dinitro-N,N-dipropyl-4-(trifluoromethyl) benzeneamine} and pendimethalin {N-(1-ethylpropyl)-3,4-dimethyl-2,6-dinitrobenzeneamine}, pendimethalin being most preferred), a phenoxy herbicide, such as 2,4-D or dicamba; a hydroxybenzonitrile herbicide such as bromoxynil or ioxynil, or an agriculturally acceptable salt or ester thereof; glyphosate or a salt thereof (e.g the isoproylamine or trimesium salt); ureas such as diuron or isoproturon; or sulfonylureas such as nicosulfuron or rimsulfuron. Where an additional pesticide is present the composition may also include a safener for the said pesticide. examples of which are described in the literature. Examples of safeners which may be present include benzyl 2-chloro-4-trifluoromethyl-1,3-thiazole-5-carboxylate (flurazole); 2,2,5,-trimethyl-N-dichloroacetyl oxazolidine (R-29148); 2,2-dimethyl-5-(2-furanyl)-N-dichloroacetyl oxazolidine (furilazole): N,N-diallyl dichloroacetamide (dichlormid); and 4-(dichloroacetyl)-3,4-dihydro-3-methyl-2H-1,4-benzoxazine (benoxacor);

The following non-limiting Example illustrates the invention.

EXAMPLE

Compositions containing a representative alkyl 4-benzoylisoxazole-3-carboxylate derivative. Compound A, were prepared and their stability analyzed. To determine the stability, the formulations were placed in 10–20 ml glass vials, scaled to prevent any solvent loss; stored at the specified temperature for the specified length of time then removed, allowed to cool to room temperature, sampled and analyzed. The method of analysis was as follows. Each formulation mixture was analyzed for the proportion of Compound A present using standard High Performance Liquid Chromatography (HPLC) technology. This involves weighing a known amount of sample into a solvent system of acetonitrile water followed by injecting a known aliquot into the HPLC system. If the method calls for an internal standard in which to calibrate accuracy, then the internal standard is added to the extracted aliquot. The extracted sample is passed through a column (either a Zorbax{trade mark} C-18 or Phenyl column) packed with sorbent. Following elution the various components of the composition are separated depending upon varying sorption capacities/hydrophilicity. The amount of the component is determined by the amount of ultraviolet light. The amount of degradation is calculated based upon the difference between the initial and stored analyzed component content.

Solutions containing 10% by weight of Compound A in N-alkylpyrrolidinones were prepared and were are stored at 54° C. for 14 days and the percentage degradation was determined according to the procedures described above.

The results were as follows:

| Solvent | % Degradation |
| --- | --- |
| N-Octyl pyrrolidinone | 2.1 |
| NMP | 2.9 |

By comparison, a composition containing isoxaflutole, which is 5-cyclopropyl-4-(2-methylsulfonyl-4-trifluoromethyl)benzoylisoxazole (25 g in 1000 ml of NMP) showed a 37% degradation after 24 hours at 20° C. Also a composition containing 25 g isoxaflutoic. 100 ml acetic acid, 100 ml of NMP, 775 ml of Exxate 700 (trade mark, an aromatic solvent) showed 21% degradation of isoxaflutole after 72 hours at 0° C., and 72% degradation after a further 72 hours at 54° C. This clearly illustrates the improved stability characteristics of the compositions of the invention.

The compositions of the invention are useful as herbicides and according to a further feature of the present invention, there is provided a method of controlling the growth of weeds at a locus which comprises applying to said locus a herbicidalily effective amount of a composition as defined above.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

We claim:

1. A liquid composition comprising:
   (a) a herbicidally effective amount of at least one alkyl 4-benzoylisoxazole-3-carboxylate derivative; and
   (b) at least one N-alkylpyrrolidinone derivative;
   said composition being substantially stable.

2. A composition according to claim 1 in which (b) is N-octylpyrrolidinone or N-methylpyrrolidinone.

3. A composition according to claim 1 in which (a) is an alkyl 4-benzoylisoxazole-3-carboxylate derivative having the general formula (I):

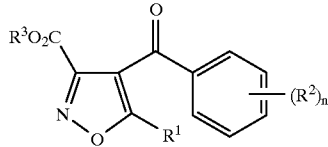

(I)

wherein
   $R^1$ is $C_{1-6}$ alkyl or $C_{3-6}$ cycloalkyl optionally substituted by $C_{1-6}$ alkyl;
   $R^2$ is selected from halogen, nitro, $-S(O)_pR^6$, $-(CR^4R^5)_q S(O)_pR^6$, $-N(R^7)SO_2R^6$, $C_{1-6}$ alkoxy, $-OSO_2R^6$, $C_{1-6}$ haloalkoxy, $C_{1-6}$ alkyl and $C_{1-6}$ haloalkyl;
   n is one, two or three; p is zero, one or two;
   $R^3$ is $C_{1-6}$ alkyl;
   $R^4$ and $R^5$ independently are hydrogen or $C_{1-4}$ alkyl;
   q is one or two; when q is two the groups $-(CR^4R^5)-$ may be the same or different;
   $R^6$ is $C_{1-6}$ alkyl, or phenyl optionally bearing from one to five substituents which may be the same or different selected from halogen, $C_{1-6}$ alkyl, $C_{1-6}$ alkoxy, $C_{1-6}$ haloalkyl, $C_{1-6}$ haloalkoxy, nitro and $-S(O)_pCH_3$;
   and $R^7$ is hydrogen or $C_{1-6}$ alkyl;
   or an agriculturally acceptable salt thereof.

4. A composition according to claim 3 in which $R^1$ is cyclopropyl and $R^2$ is halogen, $-S(O)_pMe$, trifluoromethyl, $C_{1-4}$ haloalkoxy, $C_{1-4}$ alkoxy or $-CH_2S(O)_pMe$.

5. A composition according to claim 4 in which the compound of formula (I) is ethyl 5-cyclopropyl-4-(2-methylsulfonyl-4-trifluoromethyl)benzoylisoxazole-3-carboxylate or ethyl 5-cyclopropyl-4-(3,4-dichloro-2-methylsulfenyl)benzoylisoxazole-3-carboxylate.

6. A composition according to claim 1 in which the pH of a 1% solution of said composition in distilled water is from about 4 to about 8.

7. A composition according to claim 1 in which the composition is an emulsifiable concentrate.

8. A composition according to claim 7 which comprises a primary solvent which is a polar solvent.

9. A composition according to claim 8 in which the primary solvent is a ketone.

10. A composition according to claim 8 which further comprises at least one secondary solvent.

11. A composition according to claim 10 which further comprises a surfactant.

12. A method for controlling the growth of weeds at a locus which comprises applying to said locus a composition as defined in claim 1.

13. A composition in the form of an emulsifiable concentrate comprising:
   (a) a herbicidally effective amount of ethyl 5-cyclopropyl-4-(2-methylsulfonyl-4-trifluoromethyl) benzoylisoxazole-3-carboxylate; and
   (b) at least one of N-octylpyrrolidinone and N-methylpyrrolidinone;
   said composition being substantially stable, wherein the pH of a 1% solution of said composition in distilled water is from about 4 to about 8.

14. A method for controlling the growth of weeds at a locus which comprises applying to said locus a composition as defined in claim 13.

* * * * *